United States Patent
Kinoshita et al.

(10) Patent No.: US 10,016,139 B2
(45) Date of Patent: Jul. 10, 2018

(54) BLOOD PRESSURE MEASUREMENT APPARATUS AND PULSE WAVE DETECTION METHOD

(71) Applicant: OMRON HEALTHCARE Co., Ltd., Kyoto (JP)

(72) Inventors: Hiroyuki Kinoshita, Kyoto (JP); Hironori Sato, Kyoto (JP); Toshihiko Ogura, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 297 days.

(21) Appl. No.: 14/667,224

(22) Filed: Mar. 24, 2015

(65) Prior Publication Data

US 2015/0190064 A1 Jul. 9, 2015

Related U.S. Application Data

(63) Continuation of application No. PCT/JP2013/070621, filed on Jul. 30, 2013.

(30) Foreign Application Priority Data

Sep. 25, 2012 (JP) ................................. 2012-211138

(51) Int. Cl.
*A61B 5/02* (2006.01)
*A61B 5/022* (2006.01)
(Continued)

(52) U.S. Cl.
CPC .......... *A61B 5/02225* (2013.01); *A61B 5/024* (2013.01); *A61B 5/02108* (2013.01);
(Continued)

(58) Field of Classification Search
CPC .............. A61B 5/02225; A61B 5/7217; A61B 5/02141; A61B 5/02233; A61B 5/02108;
(Continued)

(56) References Cited

U.S. PATENT DOCUMENTS 5,054,494 A * 10/1991 Lazzaro ............... A61B 5/7242
600/490
5,094,245 A 3/1992 Shirasaki
(Continued)

FOREIGN PATENT DOCUMENTS

JP H04-364827 A 12/1992
JP 2002-532120 A 10/2002
(Continued)

OTHER PUBLICATIONS

International Search Report issued in corresponding International Application No. PCT/JP2013/070621 dated Aug. 27, 2013, and English translation thereof (4 pages).

*Primary Examiner* — Navin Natnithithadha
*Assistant Examiner* — Andrey Shostak
(74) *Attorney, Agent, or Firm* — Osha Liang LLP

(57) ABSTRACT

The blood pressure measurement apparatus includes a pressure sensor that detects the pressure in a cuff and outputs a cuff pressure signal, and a pulse wave detection unit that detects a pulse wave in the cuff pressure signal. The pulse wave detection unit includes an analog HPF that extracts a high-frequency component from the cuff pressure signal, an A/D conversion unit, a signal storage unit that stores a signal obtained by performing A/D conversion on the cuff pressure signal detected at the time when the pressurizing pressure changes from increasing to decreasing, a subtraction unit that subtracts the signal stored by the signal storage unit from an output signal of the A/D conversion unit, and a digital HPF that extracts a high-frequency component from the output signal of the subtraction unit.

16 Claims, 11 Drawing Sheets

(51) Int. Cl.
 *A61B 5/024* (2006.01)
 *A61B 5/00* (2006.01)
 *A61B 5/021* (2006.01)
(52) U.S. Cl.
 CPC ...... *A61B 5/02141* (2013.01); *A61B 5/02233* (2013.01); *A61B 5/7217* (2013.01); *A61B 5/7225* (2013.01)
(58) Field of Classification Search
 CPC ... A61B 5/024; A61B 5/7225; H03H 17/0219
 See application file for complete search history.

(56) References Cited

U.S. PATENT DOCUMENTS

| | | | | |
|---|---|---|---|---|
| 5,594,612 A * | 1/1997 | Henrion | ............. | H03M 1/1038 324/620 |
| 6,155,983 A * | 12/2000 | Kosuda | ................ | A61B 5/024 600/485 |
| 7,286,871 B2 * | 10/2007 | Cohen | ................ | A61B 5/04004 600/300 |
| 2005/0256412 A1 * | 11/2005 | Shimazu | ................ | A61B 5/022 600/500 |
| 2011/0172504 A1 * | 7/2011 | Wegerich | ............. | A61B 5/0205 600/301 |
| 2011/0184297 A1 * | 7/2011 | Vitali | ................ | A61B 5/04017 600/509 |
| 2011/0213205 A1 * | 9/2011 | Uchiyama | .......... | A61B 1/00009 600/118 |

FOREIGN PATENT DOCUMENTS

| | | |
|---|---|---|
| JP | 2003-070755 A | 3/2003 |
| JP | 2003-180640 A | 7/2003 |
| JP | 2008-237519 A | 10/2008 |

* cited by examiner

ANALOG HPF OUTPUT

DEFLATION START

BASELINE
COMPONENT

DEFLATION START

PULSE WAVE
COMPONENT

DEFLATION START

BLOOD PRESSURE MEASUREMENT APPARATUS AND PULSE WAVE DETECTION METHOD

TECHNICAL FIELD

The present invention relates to an oscillometric blood pressure measurement apparatus and a pulse wave detection method.

BACKGROUND ART

An oscillometric blood pressure measurement apparatus (e.g., see Patent Documents 1 to 3) is known as an apparatus that automatically measures a body's blood pressure value.

An oscillometric automatic blood pressure measurement apparatus slowly changes the pressure with which a cuff wrapped around a part of a body pressurizes the body (cuff pressure) at a predetermined speed, and detects the pressure in the cuff while the pressurizing pressure is being changed. Also, a pulse wave, which is a pressure component that is superimposed on the cuff pressure in synchronization with the body's pulse, is detected in the detected pressure in the cuff, and the body's blood pressure value is determined based on the change in the amplitude of the pulse wave.

Patent Documents 1 and 2 disclose automatic blood pressure measurement apparatuses that detect a pulse wave by passing a cuff pressure detection signal through an analog high-pass filter or a digital high-pass filter and calculate the blood pressure value based on the amplitude of the detected pulse wave.

With this type of automatic blood pressure measurement apparatus, rapid change occurs in the cuff pressure detection signal in a process of changing from a step of increasing the cuff pressure to a step of reducing the cuff pressure. For this reason, in Patent Documents 1 and 2, a transient response period occurs in the output of the analog high-pass filter or the digital high-pass filter due to this change, and during the transient response period, the amplitude of the pulse wave cannot be detected accurately.

Note that if a high-order filter is used or the filter is constituted by multiple stages, the transient response period can be shortened to the extent that the accuracy of measuring the blood pressure is not influenced. However, high-order filters and multi-stage filters are high in cost.

In view of this, in Patent Document 3, in order to prevent a decrease in the blood pressure measurement accuracy and a decrease in the blood pressure measurement speed due to the transient response, a transient response period generated in the digital high-pass filter during a switch from increasing to decreasing the cuff pressure is eliminated by inputting a ramp signal into the filter and thereby resetting the filter.

CITATION LIST

Patent Literature

Patent Document 1: JP 2003-70755A
Patent Document 2: JP H4-364827A
Patent Document 3: JP 2002-532120A

SUMMARY OF INVENTION

However, with the method disclosed in Patent Document 3, a ramp signal needs to be generated, and therefore the influence of the transient response cannot be eliminated easily.

Therefore, one or more embodiments of the claimed invention provides a blood pressure measurement apparatus and a pulse wave detection method, according to which the influence of a transient response of a filter can be reduced with a lower-cost configuration, and a blood pressure value can be measured at a high accuracy.

A blood pressure measurement apparatus according to one or more embodiments of the claimed invention includes: a cuff configured to be attached at a measurement site of a body; a pressurizing pressure adjustment unit configured to change a pressure with which the cuff pressurizes the measurement site; a cuff pressure detection unit configured to detect the pressure in the cuff in a period of changing the pressurizing pressure and output an analog cuff pressure signal; a pulse wave detection unit configured to detect, in the cuff pressure signal, a pulse wave, which is a pressure component that is superimposed on the pressurizing pressure in synchronization with the body's pulse; and a blood pressure determination unit configured to determine a measured blood pressure value using an amplitude value of the pulse wave detected by the pulse wave detection unit, wherein the pulse wave detection unit includes an analog filter configured to extract a high-frequency component from the cuff pressure signal, an A/D conversion unit configured to perform digital conversion on an output signal of the analog filter, a subtraction processing unit configured to perform subtraction processing on an output signal of the A/D conversion unit, and a digital filter configured to perform filter processing for extracting a high-frequency component on the signal resulting from the subtraction processing performed by the subtraction processing unit, and the subtraction processing unit performs at least one of first subtraction processing in which a first signal, which is a signal resulting from the cuff pressure signal passing through the A/D conversion unit at a first time, which is any time in a period starting from an increase start time at which the pressurizing pressure starts increasing and ending at a time at the elapse of a pre-determined amount of time since the increase start time, is subtracted from an output signal resulting from the cuff pressure signal passing through the A/D conversion unit in a period from the first time to a decrease start time at which the pressurizing pressure changes from increasing to decreasing, and second subtraction processing in which a second signal, which is a signal resulting from the cuff pressure signal passing through the A/D conversion unit at a second time, which is any time in a period from the decrease start time to a time at the elapse of a predetermined amount of time since the decrease start time, is subtracted from an output signal resulting from the cuff pressure signal passing through the A/D conversion unit after the second time.

The pulse wave detection method according to the one or more embodiments of the claimed invention includes: a pressurizing pressure adjustment step of changing a pressure with which a cuff attached at a measurement site of a body pressurizes the measurement site; a cuff pressure detection step of detecting pressure in the cuff in a period of changing the pressurizing pressure as an analog cuff pressure signal; and a pulse wave detection step of detecting, in the cuff pressure signal, a pulse wave, which is a pressure component that is superimposed on the pressurizing pressure in synchronization with a pulse of the body, wherein the pulse wave detection step includes a step of extracting a high-frequency component from the cuff pressure signal by passing the cuff pressure signal through an analog filter, a step of converting, into a digital signal, the cuff pressure signal resulting from passing through the analog filter, a subtraction processing step of performing subtraction processing on the digital signal, and a step of extracting a high-frequency component by performing digital filter processing on a signal resulting from the processing of the subtraction processing step, and in the subtraction processing step, at least one of first subtraction processing in which a first signal, which is a signal resulting from the cuff pressure signal passing through the A/D conversion unit at a first time, which is any time in a period from an increase start time at which the pressurizing pressure starts increasing to a time at the elapse of a pre-determined amount of time since the increase start time, is subtracted from an output signal resulting from the cuff pressure signal passing through the A/D conversion unit in a period from the first time to a decrease start time at which the pressurizing pressure changes from increasing to decreasing, and second subtraction processing in which a second signal, which is a signal resulting from the cuff pressure signal passing through the A/D conversion unit at a second time, which is any time in a period from the decrease start time to a time at the elapse of a predetermined amount of time since the decrease start time, is subtracted from an output signal resulting from the cuff pressure signal passing through the A/D conversion unit after the second time.

Advantageous Effects of the Invention

According to one or more embodiments of the claimed invention, it is possible to provide a blood pressure measurement apparatus and a pulse wave detection method according to which it is possible to perform measurement of a blood pressure value at a high accuracy by causing a transient response of a filter to converge rapidly with a low cost.

DESCRIPTION OF EMBODIMENTS

Hereinafter, embodiments of the claimed invention will be described with reference to the drawings.

Figure 1:
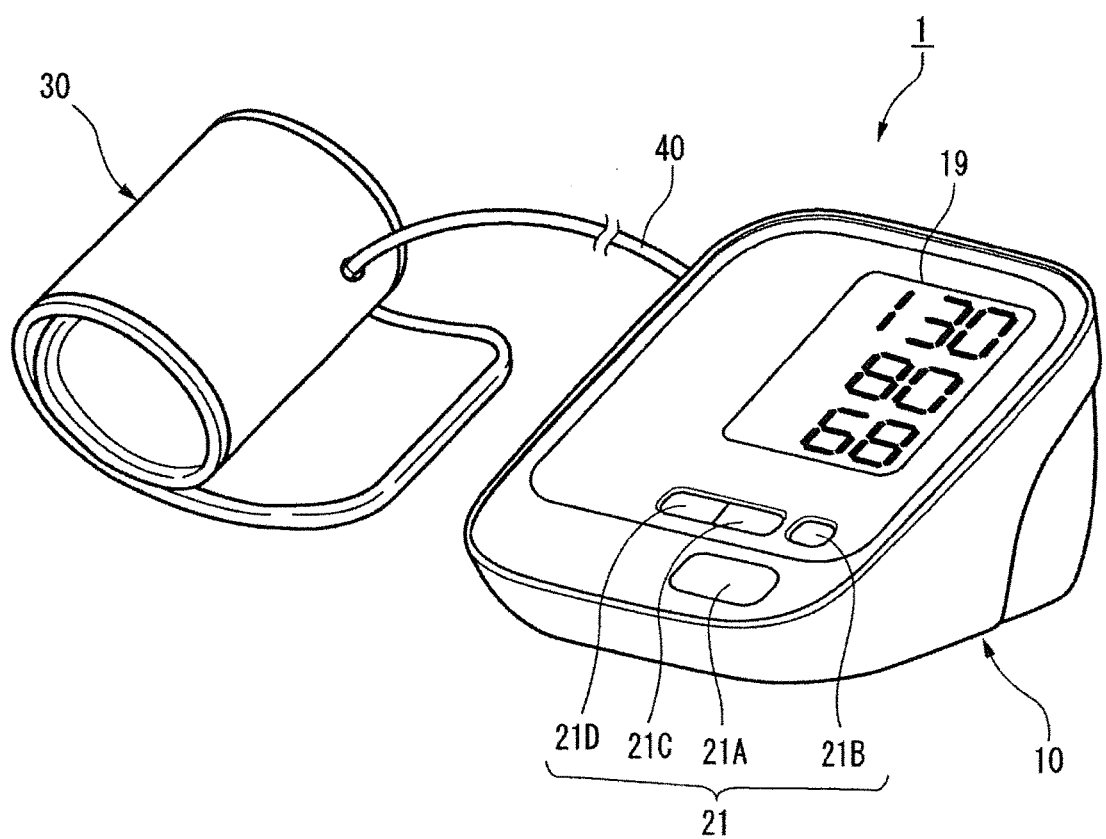
FIG. 1 is an external appearance diagram showing an overall configuration of a blood pressure measurement apparatus, for describing an embodiment of the claimed invention.

FIG. 1 is an external appearance diagram showing an overall configuration of a blood pressure measurement apparatus, for describing an embodiment of the claimed invention.

A blood pressure measurement apparatus 1 includes a main body portion 10, a cuff 30 that can be wrapped around a measurement subject's upper arm, and an air tube 40 connecting the main body portion 10 and the cuff 30. The cuff 30 includes an air bladder 31 (see FIG. 2), and the air tube 40 shown in FIG. 1 is connected to the air bladder 31.

In the present specification, "cuff" refers to a belt-shaped or tube-shaped structure that has an inner cavity and can be wrapped around a measurement site of a body (e.g., upper arm, wrist, etc.), and it indicates an object that is used to measure blood pressure by pressurizing an artery of a measurement subject by insertion of a fluid such as air or a liquid into the inner cavity.

The word "cuff" refers to a concept that includes a fluid bladder and a wrapping means for wrapping the fluid bladder around a body. It is also called an arm band in some cases. In the example shown in FIG. 1, the cuff 30 and the main body portion 10 are separate, but the cuff 30 and the main body portion 10 may be integrated.

The main body portion 10 includes a display unit 19 that is constituted by liquid crystal or the like for displaying various types of information such as a blood pressure value, a pulse rate, and the like, and an operation unit 21 that includes multiple switches 21A, 21B, 21C, and 21D for receiving instructions from a user (measurement subject).

The operation unit 21 includes a measure/stop switch 21A that receives input of an instruction for switching a power supply on or off and instructions for starting and stopping measurement, a memory switch 21B for receiving an instruction to read out information such as blood pressure data stored in the main body unit 10 and display it on the display unit 19, arrow switches 21C and 21D for receiving an instruction to raise or lower the memory number at the time of calling out information, and the like.

Figure 2:
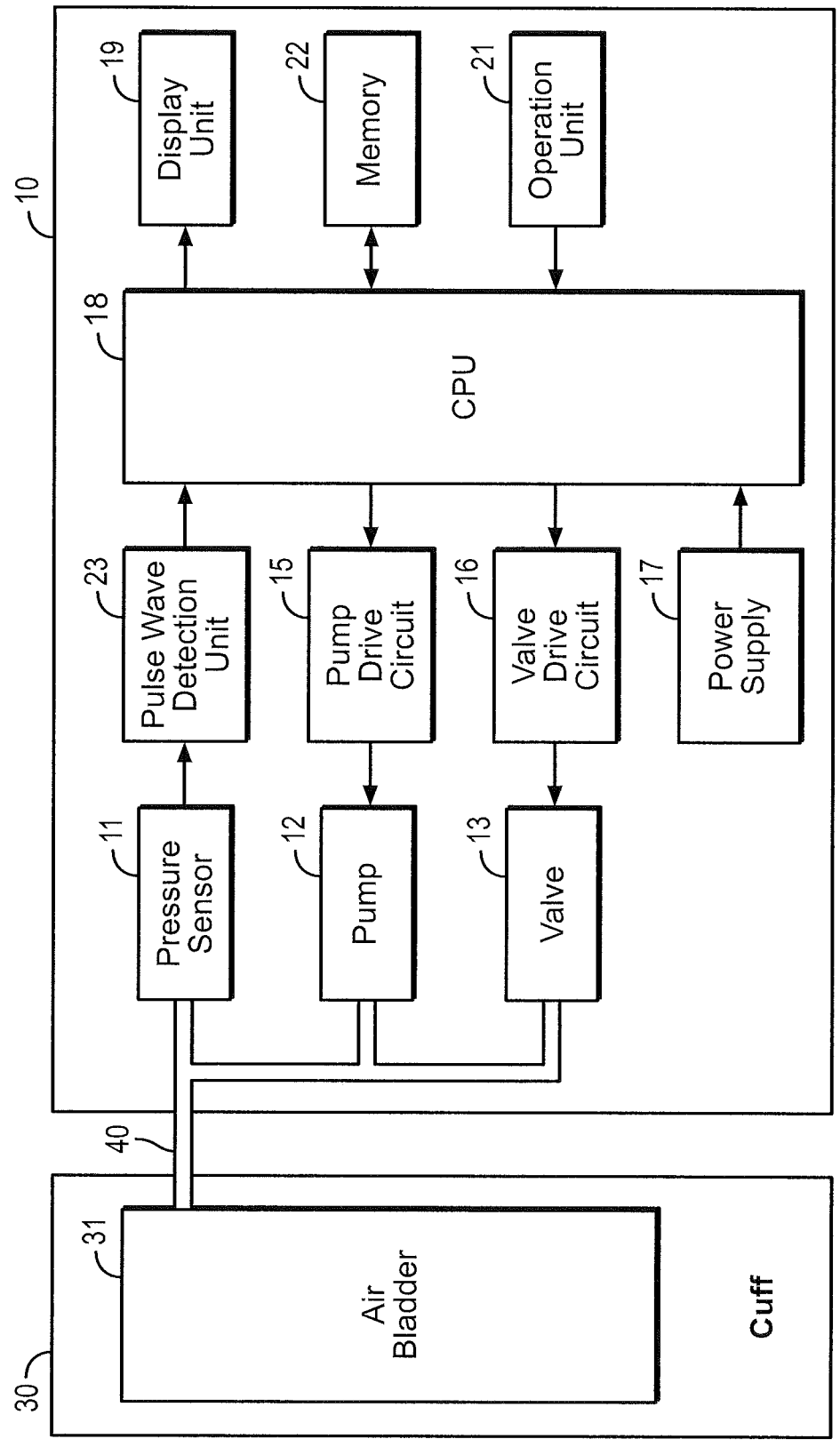
FIG. 2 is a diagram showing an internal configuration of a main body portion 10 of a blood pressure measurement apparatus 1 shown in FIG. 1.

FIG. 2 is a diagram showing an internal configuration of the main body portion 10 of the blood pressure measurement apparatus 1 shown in FIG. 1.

The main body portion 10 includes a pressure sensor 11, a pump 12, and an air discharge valve (referred to below as "valve") 13 that are connected to the air tube 40, a pulse wave detection unit 23, a pump drive circuit 15, a valve drive circuit 16, a power supply 17 that supplies power to the parts of the main body unit 10, the display unit 19, a control unit (CPU) 18 that performs overall control of the main body portion 10 and performs various types of calculation processing, an operation unit 21, and a memory 22.

The pump 12 supplies air to the air bladder 31 in order to increase the pressure with which the cuff 30 pressurizes the measurement site (hereinafter also referred to as "cuff pressure").

The valve 13 opens and closes in order to discharge or seal air in the air bladder 31.

The pump drive circuit 15 controls the driving of the pump 12 based on a control signal obtained from the CPU 18.

The valve drive circuit 16 controls the opening and closing of the valve 13 based on the control signal obtained from the CPU 18.

A pressurizing pressure adjustment unit that changes the pressure with which the cuff 30 pressurizes the measurement site is constituted by the pump 12, the valve 13, the pump driving circuit 15, and the valve driving circuit 16.

Upon the start of a blood pressure measurement operation, the pressurizing pressure adjustment unit causes the cuff pressure to gradually increase. When the cuff pressure reaches a pressure that is sufficiently greater than a maximum blood pressure, the pressurizing pressure adjustment unit causes the cuff pressure to gradually decrease, and when blood pressure measurement is complete, the valve 13 is opened and the air in the air bladder 31 is mandatorily discharged.

The pressure sensor 11 detects the pressure in the air bladder 31 of the cuff 30 and outputs the detected pressure as an analog electric signal (cuff pressure signal).

In the cuff pressure signal, which is the output signal of the pressure sensor 11, the pulse wave detection unit 23 detects a pulse wave, which is a pressure component that is superimposed on the cuff pressure in synchronization with the pulse of the body.

The memory 22 includes a ROM (Read Only Memory) that stores programs and data for causing the CPU 18 to perform predetermined operations, a RAM (Random Access Memory) serving as a work memory, and a flash memory that stores measured blood pressure data and the like.

Figure 3:
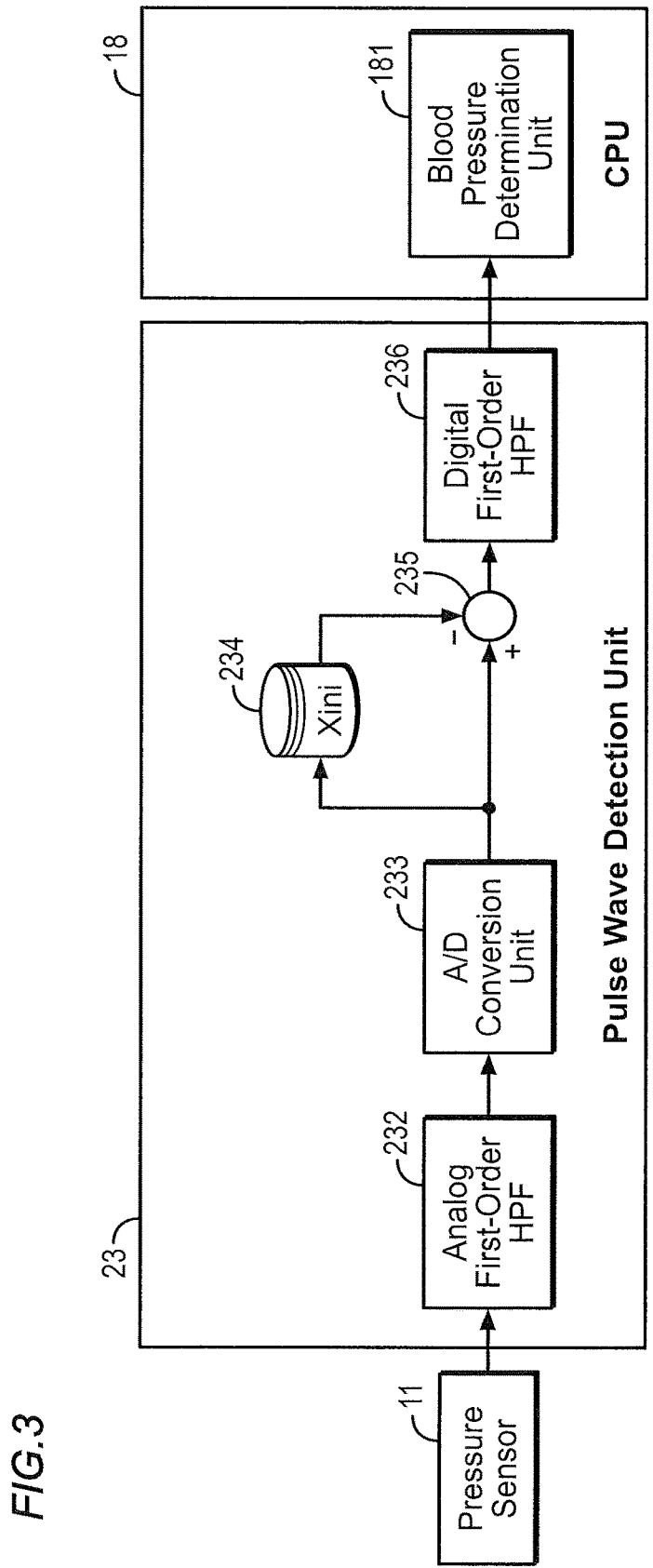
FIG. 3 is a diagram showing an internal configuration of a pulse wave detection unit 23 and a portion of the functional blocks configured by a CPU 18, shown in FIG. 2.

FIG. 3 is a diagram showing an internal configuration of the pulse wave detection unit 23 and a portion of the functional blocks configured by the CPU 18, shown in FIG. 2.

The pulse wave detection unit 23 includes a first-order analog high-pass filter (HPF) 232, an A/D conversion unit 233, a signal storage unit 234, a pulse wave subtraction unit 235, and a first-order digital high-pass filter 236.

The analog HPF 232 extracts a high-frequency component from the cuff pressure signal detected by the pressure sensor 11 and outputs it to the A/D conversion unit 233.

The frequency of the pulse wave is around 1 Hz to 10 Hz. For this reason, the cutoff frequency of the analog HPF 232 is generally set to around 0.5 Hz.

Since the analog HPF 232 is a first-order filter, signal components near 0 Hz are not attenuated much. As a result, low-frequency components (referred to below as baseline components) corresponding to variations in the cuff pressure that are generated as a result of control performed by the pressurizing pressure adjustment unit are included in the output signal of the analog HPF 232.

Note that the analog HPF 232 may be a band-pass filter instead of a high-pass filter.

In the case of using a band-pass filter, it is preferable that the band-pass filter has a property of allowing signals to pass which fall within a range of around 0.5 Hz to around 10.5 Hz. In the case of using a band-pass filter as well, signal components near 0 Hz are not attenuated, and therefore low-frequency components corresponding to variations in cuff pressure will remain.

The analog HPF 232 is not limited to being a first-order filter, but in consideration of the manufacturing cost of the blood pressure measurement apparatus 1, it is preferable to use one that is as low-order as possible.

The A/D conversion unit 233 converts the output signal of the analog HPF 232 into a digital signal.

The digital HPF 236 is a first-order filter that performs digital filter processing for extracting high-frequency components from the output signal of the A/D conversion unit 233. The cutoff frequency of the digital HPF 236 is the same as that of the analog HPF 232.

The digital HPF 236 is not limited to being a first-order filter, and in consideration of the manufacturing cost of the blood pressure measurement apparatus 1, it is preferable to use one that is as low-order as possible.

Figure 4A:
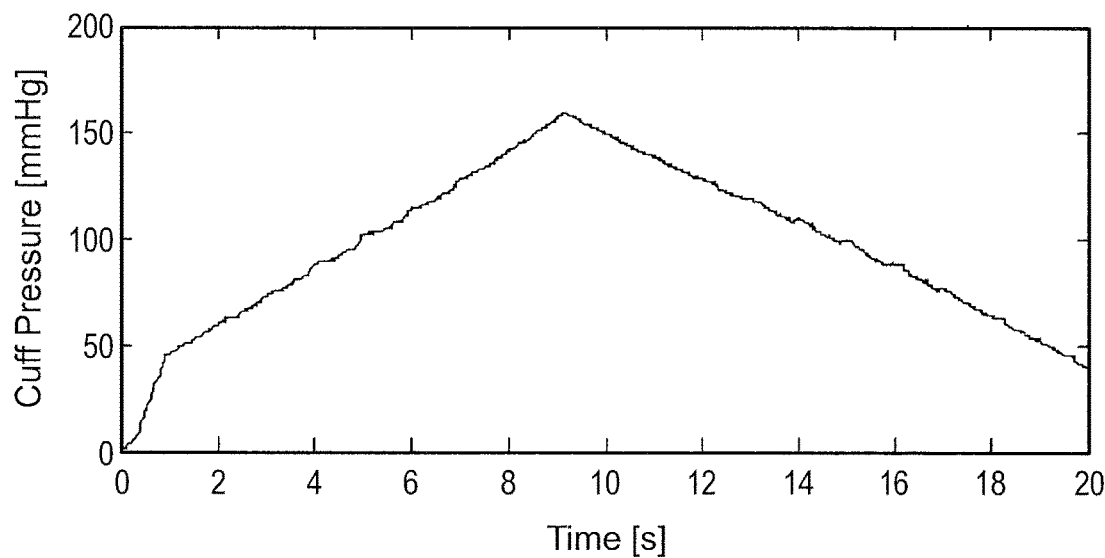
FIGS. 4A and 4B are diagrams showing a cuff pressure signal detected by a cuff pressure detection unit of the blood pressure measurement apparatus 1 shown in FIG. 1 and a signal resulting from the cuff pressure signal passing through an analog HPF.
Figure 4B:
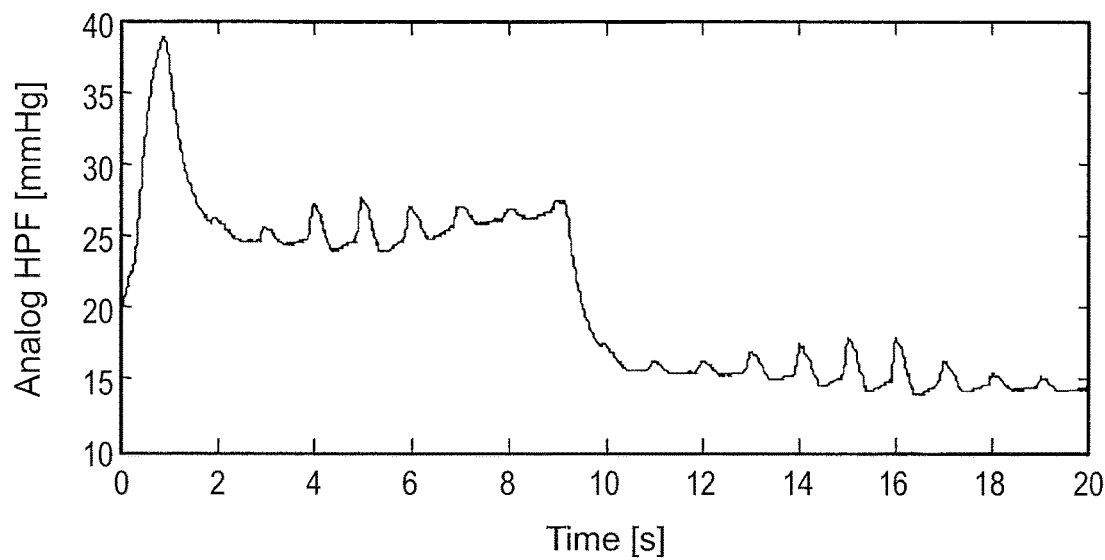

The output signal of the analog HPF 232 is as indicated in FIG. 4B of FIG. 4, for example. Note that FIG. 4A of FIG. 4 shows the cuff pressure signal detected by the pressure sensor 11.

As shown in FIG. 4B, the output signal of the analog HPF 232 includes the low-frequency components corresponding to the variations in the cuff pressure, and therefore for a predetermined amount of time after the timings when the cuff pressure changes rapidly (in the example shown in FIG. 4, the times 0 and 9 (in seconds)), transient response periods are generated in which the output of the filter varies significantly.

Figure 5A:
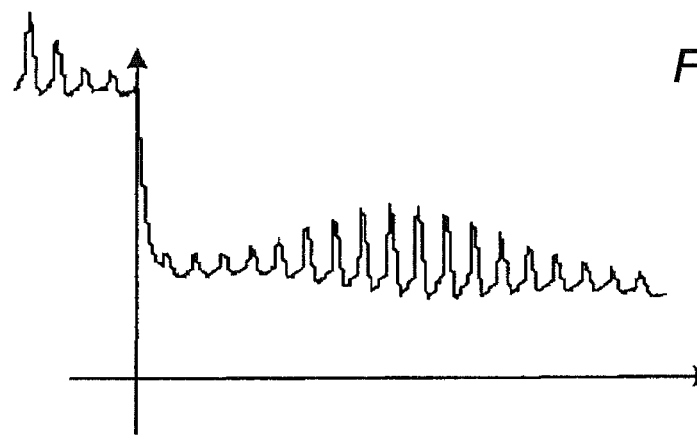
FIGS. 5A, 5B, and 5C are diagrams showing a signal resulting from passing through an analog HPF of the blood pressure measurement apparatus 1 shown in FIG. 1.
Figure 5B:
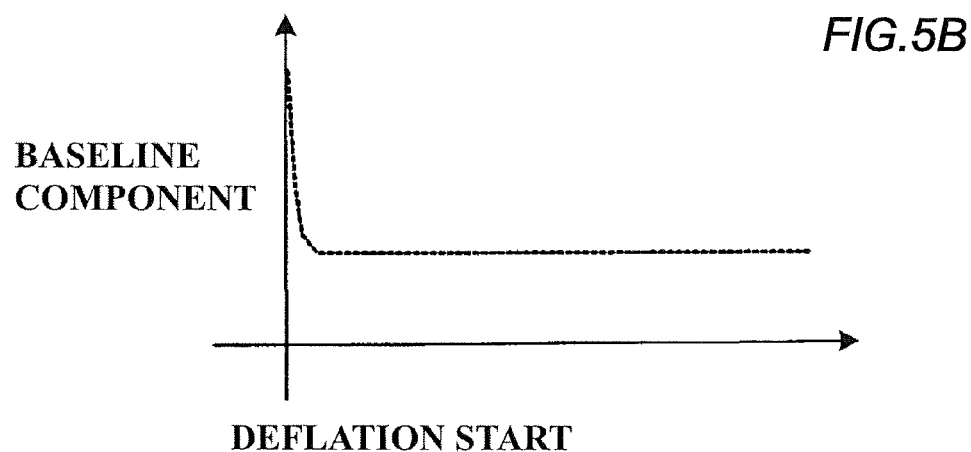
Figure 5C:
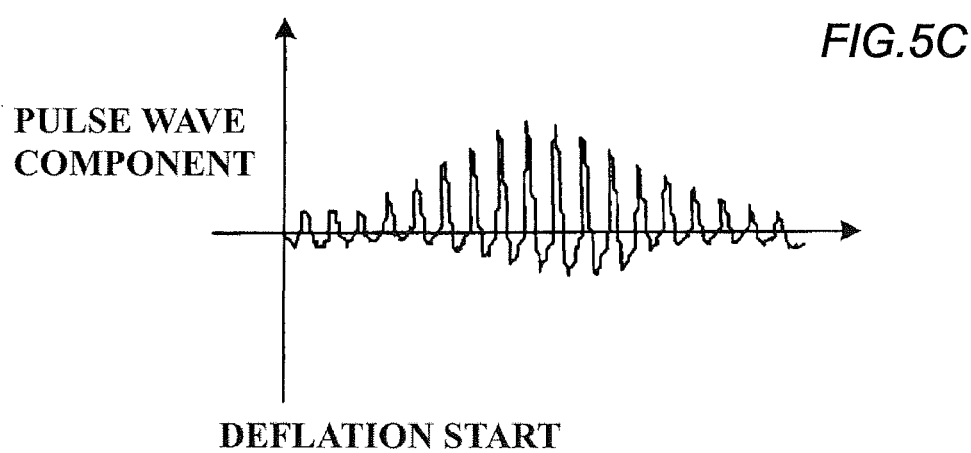

FIG. 5A of FIG. 5 shows an output signal waveform of the analog HPF 232 when the cuff pressure deflation start time in FIG. 4 is taken as the origin. The waveform shown in FIG. 5A can be divided into a waveform for low-frequency components (baseline components) corresponding to the variation in the cuff pressure (FIG. 5B of FIG. 5) and into a waveform for the pulse wave (FIG. 5C of FIG. 5).

Here, when the waveform for the low-frequency baseline component shown in FIG. 5B is input into the digital HPF 236, a transient response occurs in the digital HPF 236, similarly to the case of using the analog HPF 232. For this reason, during the transient response, the amplitude of the pulse wave can not be detected accurately.

In view of this, the blood pressure measurement apparatus 1 is provided with a signal storage unit 234 and a pulse wave subtraction unit 235, and it is thereby possible to shorten the transient response period of the digital HPF 236.

During the period from when the cuff pressure starts increasing to when the cuff pressure starts to decrease, the signal storage unit 234 stores a cuff pressure signal that was detected by the pressure sensor 11 at the time when the cuff pressure starts to increase, the cuff pressure signal having passed through the analog HPF 232 and the A/D conversion unit 233. Also, following the time when the cuff pressure changes from increasing to decreasing, the signal storage unit 234 stores the cuff pressure signal that was detected by the pressure sensor 11 at that time (transient response start time), the cuff pressure signal having passed through the analog HPF 232 and the A/D conversion unit 233.

The pulse wave subtraction unit 235 subtracts the output signal stored in the signal storage unit 234 from the output signal of the A/D conversion unit 233 and inputs the output signal resulting from the subtraction into the digital HPF 236.

With the provision of the pulse wave subtraction unit 235, the digital HPF 236 performs a filter calculation expressed by the following equation.

$$Y_n = a1 \times (X_n - X_{ini}) + a2 \times (X_{n-1} - X_{ini}) + b1 \times Y_{n-1}$$

$Y_n$: Output of digital HPF 236 at time n $X_n - X_{ini}$: Input to digital HPF 236 at time n $X_{ini}$: Digital HPF input value at cuff pressure increase start time or cuff pressure decrease start time (value stored in signal storage unit 234)

a1, a2, b1: Filter coefficients

Thus, upon the input value of the digital HPF 236 at the timing at which the cuff pressure changes significantly being set to 0, the calculation for digital filter processing can be started.

In other words, when the baseline component in the step in which pressure is applied to the arm by the cuff (inflation step) and the baseline component in the step in which the pressure of the cuff on the arm is reduced (deflation step) are caused to rapidly converge, digital filter processing can be started, and a transient response can be prevented from occurring in the digital HPF 236.

Figure 6:
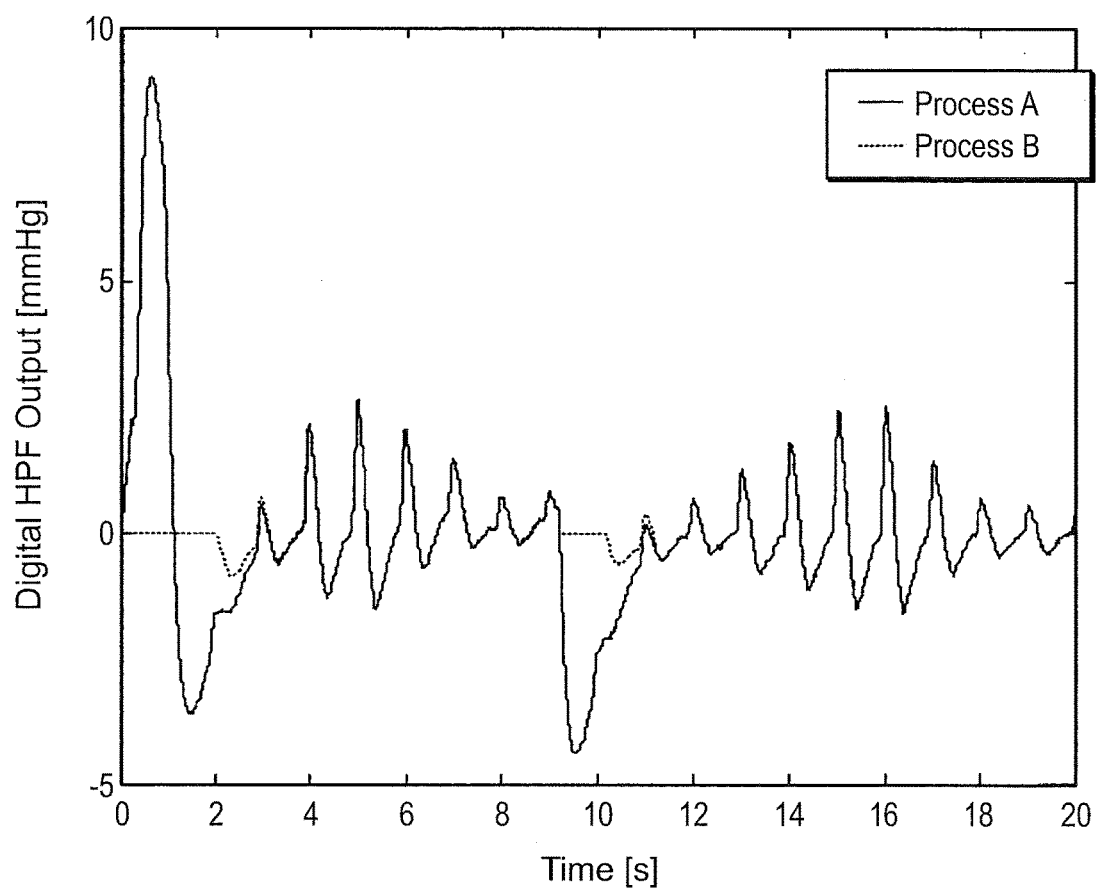
FIG. 6 is a diagram showing an output waveform resulting from filter processing performed by a digital HPF 236.

FIG. 6 is a diagram showing an output waveform resulting from filter processing performed by the digital HPF 236.

The waveform indicated by the solid line in FIG. 6 is the waveform in the case where the output signal of the A/D conversion unit 233 has been directly input into the digital HPF 236 (the case where $X_{ini}=0$ in the equation above). The waveform indicated by the broken line in FIG. 6 is the waveform in the case where the output signal of the A/D conversion unit 233 has been input into the digital HPF 236 after the subtraction by the pulse wave subtraction unit 235.

As shown in FIG. 6, by performing subtraction processing using the pulse wave subtraction unit 235, it is possible to shorten the transient response period from the start of the increase of the cuff pressure and the transient response period from the start of the decrease of the cuff pressure.

The CPU 18 functions as a blood pressure determination unit 181 by reading out and executing a program stored in the memory 22.

The blood pressure determination unit 181 calculates the amplitude of a pulse wave based on the output signal of the digital HPF 236 obtained in the inflation step or the deflation step, and uses the amplitude value to determine the measured blood pressure value according to a known method.

Operations of the blood pressure measurement apparatus 1 with the above-described configuration will be described next.

When the measure/stop switch 21A is pressed so as to instruct the start of blood pressure measurement, the CPU 18 shuts the valve 13 and starts inflation of the cuff 30 by insertion of air into the cuff 30 using the pump 12. At the inflation start time, the cuff pressure signal (referred to as "S1"), which has been detected by the pressure sensor 11 and subjected to digital conversion, is stored in the signal storage unit 234.

Also, the pulse wave subtraction unit 235 starts processing for subtracting the cuff pressure signal S1 from the cuff pressure signal that was detected by the pressure sensor 11 after the inflation start time and passed through the analog HPF 232 and the A/D conversion unit 233, and the cuff pressure signal obtained by subtraction is input into the digital HPF 236 and subjected to digital filter processing.

When the cuff pressure reaches a value that is significantly greater than the maximum blood pressure, the CPU 18 stops inflation by means of the pump 12 and gradually releases the valve 13 so as to discharge the air from the air bladder 31 and thereby reduction of the cuff pressure is started.

When the cuff pressure starts to be decreased, the cuff pressure signal S1 stored in the signal storage unit 234 is erased, and a cuff pressure signal (referred to as "S2") that has been detected by the pressure sensor 11 at the deflation start time and subjected to digital conversion is stored in the signal storage unit 234.

Also, the pulse wave subtraction unit 235 starts processing for subtracting the cuff pressure signal S2 from the cuff pressure signal detected by the pressure sensor 11 after the deflation start time, the cuff pressure signal having passed through the analog HPF 232 and the A/D conversion unit 233. The cuff pressure signal resulting from the subtraction is input into the digital HPF 236 and subjected to digital filter processing.

According to the operation described above, a signal waveform such as that indicated by the broken line in FIG. 6 is output from the digital HPF 236.

The CPU 18 calculates the amplitude of the waveform based on the output signal of the digital HPF 236 and uses the amplitude value to determine the measured blood pressure value according to a known method.

When the measured blood pressure value is determined, the CPU 18 releases the valve 13 so as to mandatorily discharge the air from the air bladder 31. Also, the CPU 18 causes the determined measured blood pressure value to be displayed on the display unit 19 and ends the blood pressure measurement processing.

As described above, the blood pressure measurement apparatus 1 detects the pulse wave using the first-order analog HPF 232 and the first-order digital HPF 236 in combination, and therefore, in contrast to a configuration in which the pulse wave is detected using only an analog HPF, a high-order filter or a multi-stage filter is not needed and thus the cost can be reduced.

Also, with the configuration in which the pulse wave is detected using only a digital HPF, a pulse wave component of several mmHg is detected after the cuff pressure signal, which changes to around 0 to 300 mmHg according to the variation in the cuff pressure, is subjected to A/D conversion. For this reason, the resolution of the A/D conversion needs to be increased, which causes an increase in cost.

In contrast, with the blood pressure measurement apparatus 1, the range of the cuff pressure signal is shortened as shown in FIG. 4B due to the analog HPF 232. For this reason, it is possible to lower the resolution required by the A/D conversion unit 233 and the cost can be reduced.

Also, according to the blood pressure apparatus 1, even if a transient response occurs in the analog HPF 232, digital filter processing can be performed after using the pulse wave subtraction unit 235 to cause the baseline components to converge. For this reason, it is possible to minimize the influence of the transient response on the output of the digital HPF 236, and high-accuracy blood pressure measurement is possible by improving the calculation accuracy of the pulse wave amplitude.

Also, an effect of enabling the influence of the transient response to be reduced can be realized by merely providing the signal storage unit 234 and the pulse wave subtraction unit 235. For this reason, the above-described effect can be obtained with little cost.

Note that even if the pulse wave subtraction unit 235 performs subtraction processing, a transient response of the digital filter will remain to a certain degree.

Figure 7:
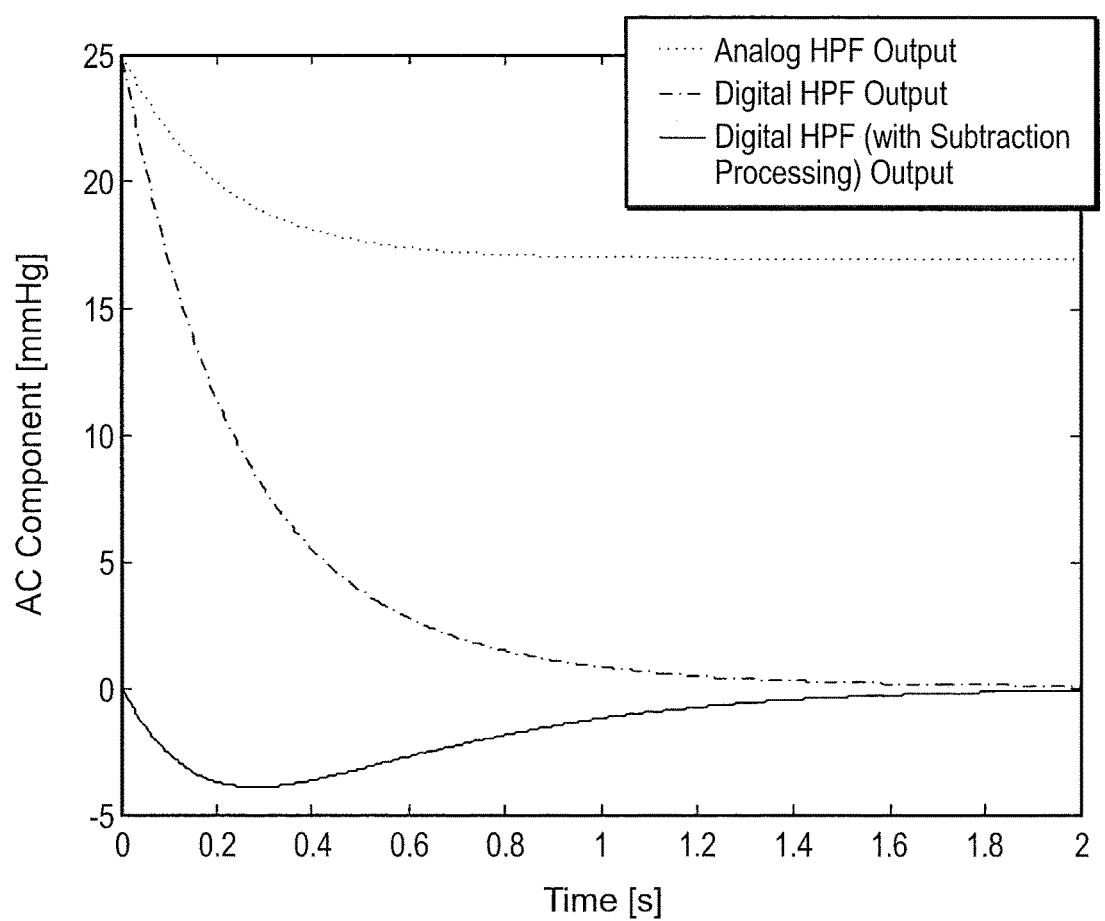
FIG. 7 is a diagram showing output of the digital HPF 236 resulting from processing performed by a pulse wave subtraction unit 235.

FIG. 7 shows a baseline component waveform (broken line), a filter output waveform (one-dot chain line) in the case where the baseline component is directly input to the digital HPF 236, and a filter output waveform (solid line) in the case where the waveform resulting from the value of the baseline component at the calculation start time (0 seconds on the horizontal axis) being subtracted from the baseline component at each time is input into the digital HPF 236.

As shown in FIG. 7, even if subtraction processing is performed, the output of the digital HPF 236 will vary slightly.

Figure 8:
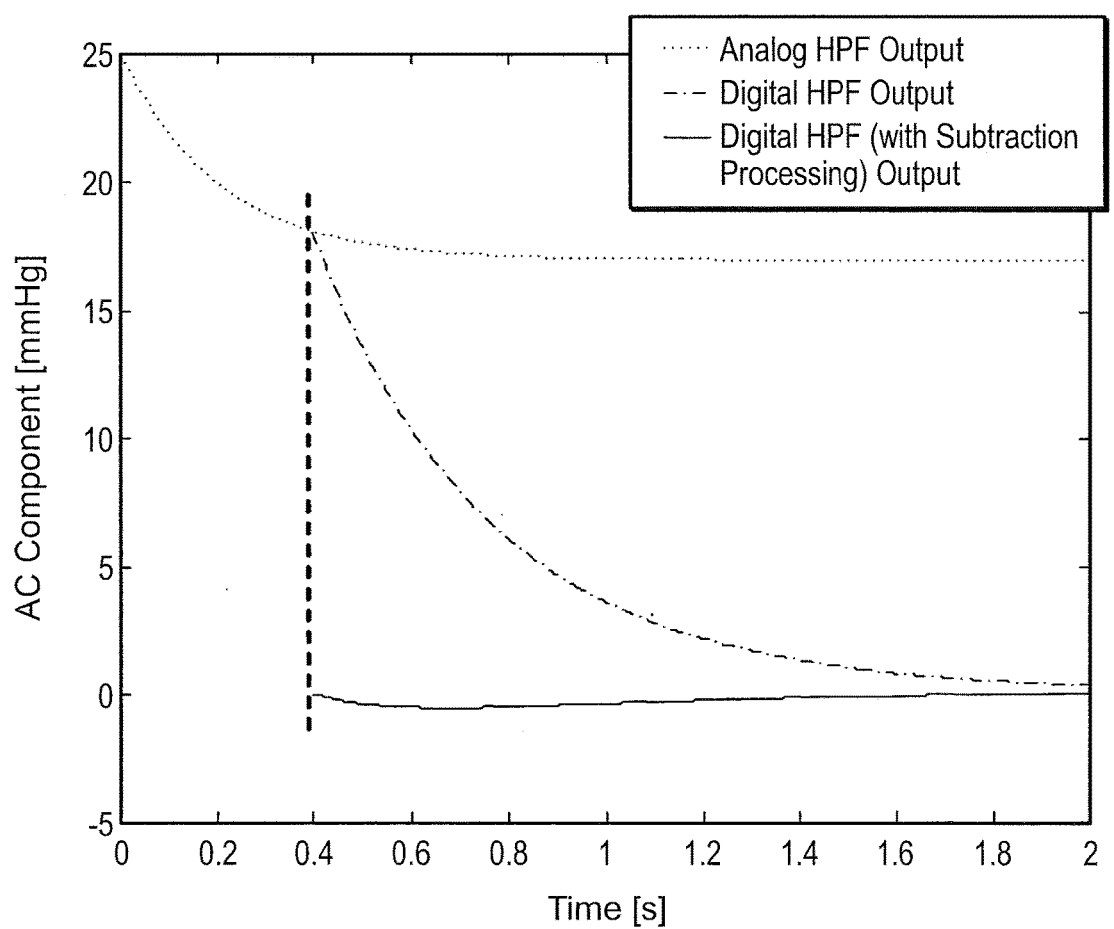
FIG. 8 is a diagram for describing an effect obtained when the digital HPF 236 is stopped for a certain amount of time.

In view of this, as shown in FIG. 8, if the digital filter processing is not performed from 0 to 0.4 seconds and digital filter processing is started using the input value at the time when time=0.4 seconds as 0, the output variation of the digital HPF 236 can be suppressed.

Figure 9:
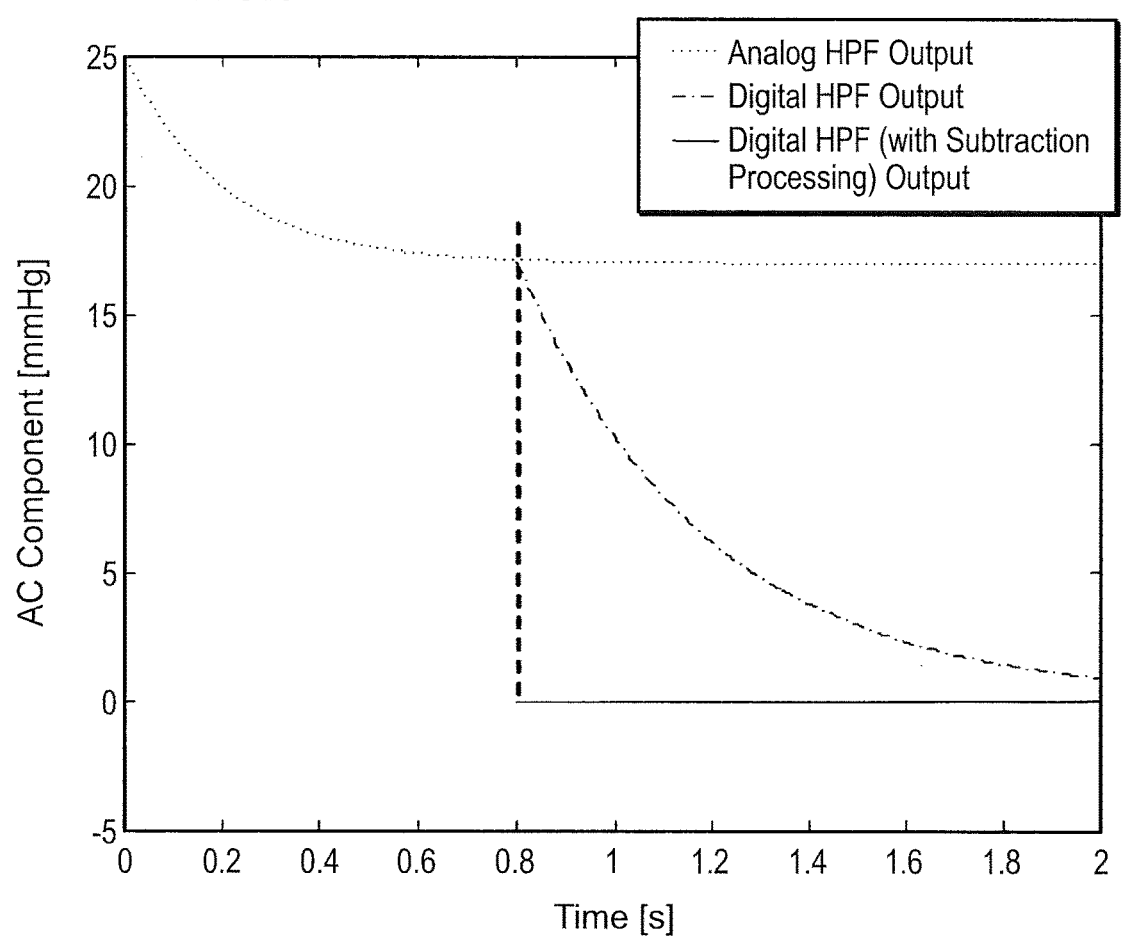
FIG. 9 is a diagram for describing an effect obtained when the digital HPF 236 is stopped for a certain amount of time.

Also, as shown in FIG. 9, if the digital filter processing is not performed from 0 to 0.8 seconds and digital filter processing is started using the input value at the time when time=0.8 seconds as 0, the output variation of the digital HPF 236 can be further suppressed.

That is to say, for a predetermined period from the start of inflation and the start of deflation, the filter processing performed by the digital HPF 236 is stopped, and upon the elapse of a certain period, the digital value of the cuff pressure signal detected at that time is stored in the signal storage unit 234. Also, the CPU 23 performs digital filter processing after subtraction processing is performed on the cuff pressure signal detected after that time, whereby it is possible to suppress variation in the output of the digital HPF 236 due to the baseline component, and it is possible to improve the blood pressure measurement accuracy.

Note that in the above-mentioned certain period, it is preferable that the signal storage unit 234 and the pulse wave subtraction unit 235 are both stopped for energy conservation.

Also, it is sufficient that the length of the certain period is an amount of time that is less than or equal to the amount of time needed for the output of the analog HPF 232 with respect to the variation in the cuff pressure to converge (transient response period of the analog HPF 232). This is because, as shown in FIG. 9, after the baseline component stabilizes, the result is the same regardless of the time at which the digital filter processing is started.

The transient response period of the analog HPF 232 depends on the design of the filter as well, and it is normally a short amount of time that is less than 1 second. Accordingly, it is possible to minimize the influence that not being able to detect the pulse wave in a certain period has on the blood pressure measurement.

Figure 10:
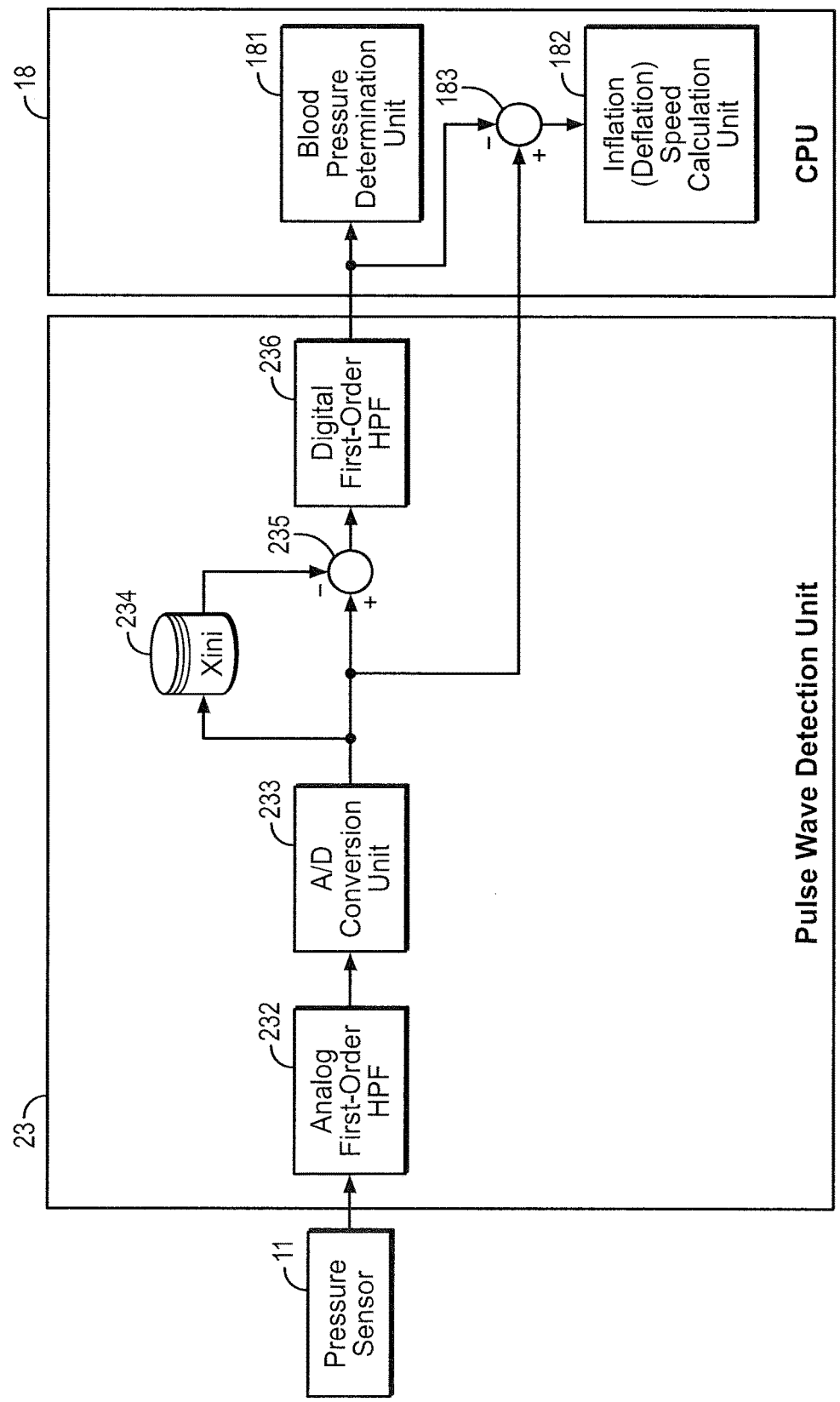
FIG. 10 is a diagram showing a modified example of the pulse wave detection unit 23 and the CPU 18 shown in FIG. 3.

FIG. 10 is a diagram showing a modified example of the pulse wave detection unit 23 and the CPU 18 shown in FIG. 3.

FIG. 10 differs from FIG. 3 in that an inflation (deflation) speed calculation unit 182 and a CPU subtraction unit 183 have been added to the CPU 18.

The inflation (deflation) speed calculation unit 182 and the CPU subtraction unit 183 are functional blocks formed by the CPU 18 executing a program.

The CPU subtraction unit 183 is provided in order to extract a baseline component included in the output of the A/D conversion unit 233.

The output of the digital HPF 236 is the pulse wave component, and the output of the A/D conversion unit 233 is the sum of the baseline component and the pulse wave component. For this reason, the CPU subtraction unit 183 can extract the baseline component by subtracting the output signal (Yn) of the digital HPF 236 from the output signal (Xn) of the A/D conversion unit 233.

In other words, the CPU subtraction unit 183 is equivalent to a first-order digital low-pass filter.

Letting K be the system gain, τ be a time constant, s be a Laplace operator, and $H_{LPF}(s)$ and $H_{HPF}(s)$ be the transfer functions for the first-order low-pass filter and the first-order high-pass filter respectively, the relationship is expressed as:

$$H_{LPF}(s)=K/(1+s\tau)$$

$$H_{HPF}(s)=Ks\tau/(1+s\tau)$$

This is also evident based on the fact that when K=1, subtracting the output of the first-order high-pass filter from the input (=1) gives the following result.

$$1-H_{HPF}(s)=1-\{s\tau/(1+s\tau)\}=1/(1+s\tau)=H_{LPF}(s)$$

The inflation (deflation) speed calculation unit 182 uses the baseline component data extracted by the CPU subtraction unit 183 (values at times when the output value is stable, not including data obtained in the transient response period of the filter) to calculate the increase speed or decrease speed of the cuff pressure.

Figure 11:
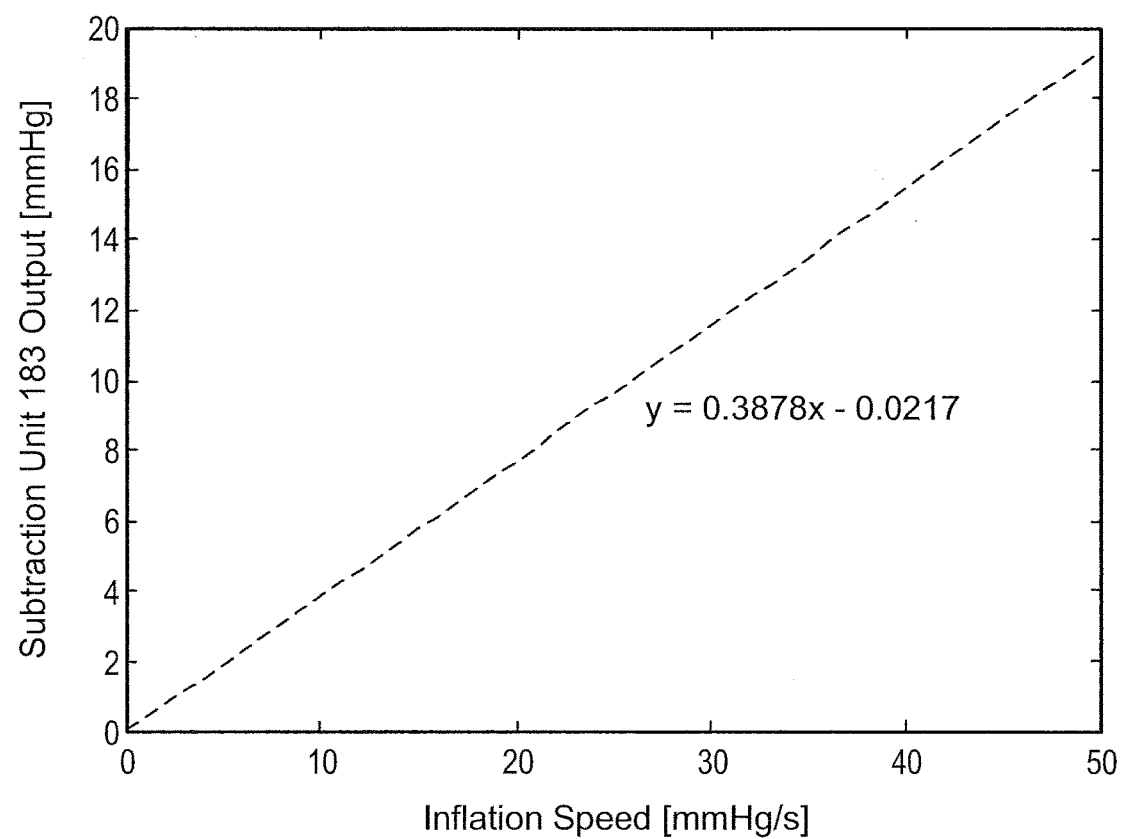
FIG. 11 is a diagram showing a relationship between baseline component data (values at times when output is stable) and cuff pressure increase speed.

FIG. 11 is a diagram showing a relationship between baseline component data (values at times when the output is stable) and the increase speed of the cuff pressure. Note that this relationship is the same for the decrease speed of the cuff pressure as well.

As shown in FIG. 11, the baseline component data and the cuff pressure change speed are in a linear relationship. For this reason, the data shown in FIG. 11 is obtained in advance and stored in the memory 22. Also, the inflation (deflation) speed calculation unit 182 calculates the increase or decrease speed of the cuff pressure at the current time based on the output signal of the CPU subtraction unit 183 and the data shown in FIG. 11.

With oscillometric blood pressure measurement, increasing or reducing the pressure with which the arm is pressurized with a constant speed is preferable for improving the accuracy of the blood pressure measurement.

With the configuration shown in FIG. 11, it is possible to calculate the speed at which the cuff pressure changes using the inflation (deflation) speed calculation unit 182. For this reason, for example, if the speed is not constant, the CPU 18 can perform feedback control so that the speed becomes constant, and can improve the blood pressure measurement accuracy.

In the present embodiment, since the analog HPF 232 is a first-order filter, a baseline component remains in the output signal of the analog HPF 232. For this reason, it is possible to extract the baseline component using the subtraction unit 237, and the baseline component can be converted into the cuff pressure change speed so as to improve the blood pressure measurement accuracy. For this reason, it is preferable that the analog HPF 232 is low-order to the extent that the baseline component remains.

In the foregoing description, it was assumed that processing was performed in which the signals stored in the signal storage unit 234 in both the cuff pressure increase period and the cuff pressure decrease period are subtracted from the output of the A/D conversion unit 233.

However, as long as the pulse wave generated in the cuff pressure decrease period is detected and the amplitude of the pulse wave is used to determine the measured blood pressure value, the operation of the signal storage unit 234, pulse wave subtraction unit 235, and digital HPF 236 may be stopped in the cuff pressure increase period. Also, it is sufficient that, at the time when the cuff pressure decrease period is entered or upon the elapse of a certain period from that time, the cuff pressure signal at that time is stored in the signal storage unit 234 and the operation of the pulse wave subtraction unit 235 and the digital HPF 236 is started.

Also, in contrast, as long as the pulse wave generated in the cuff pressure increase period is detected and the amplitude value of the pulse wave is used to determine the measured blood pressure value, the operation of the signal storage unit 234, the pulse wave subtraction unit 235, and the digital HPF 236 may be stopped in the cuff pressure decrease period.

As described above, the following items are disclosed in the present specification.

The disclosed blood pressure measurement apparatus includes: a cuff configured to be attached at a measurement site of a body; a pressurizing pressure adjustment unit configured to change the pressure with which the cuff pressurizes the measurement site; a cuff pressure detection unit configured to detect the pressure in the cuff in a period of changing the pressurizing pressure and output an analog cuff pressure signal; a pulse wave detection unit configured to detect, in the cuff pressure signal, a pulse wave, which is a pressure component that is superimposed on the pressurizing pressure in synchronization with the body's pulse; and a blood pressure determination unit configured to determine a measured blood pressure value using the amplitude value of the pulse wave detected by the pulse wave detection unit, wherein the pulse wave detection unit includes an analog filter configured to extract a high-frequency component from the cuff pressure signal, an A/D conversion unit configured to perform digital conversion on an output signal of the analog filter, a subtraction processing unit configured to perform subtraction processing on an output signal of the A/D conversion unit, and a digital filter configured to perform filter processing for extracting a high-frequency component on the signal resulting from the subtraction processing performed by the subtraction processing unit, and the subtraction processing unit performs at least one of first subtraction processing in which a first signal, which is a signal resulting from the cuff pressure signal passing through the A/D conversion unit at a first time, which is any time in a period from an increase start time at which the pressurizing pressure starts increasing to a time at the elapse of a pre-determined amount of time since the increase start time, is subtracted from an output signal resulting from the cuff pressure signal passing through the A/D conversion unit in a period from the first time to a decrease start time at which the pressurizing pressure changes from increasing to decreasing, and second subtraction processing in which a second signal, which is a signal resulting from the cuff pressure signal passing through the A/D conversion unit at a second time, which is any time in a period from the decrease start time to a time at the elapse of a predetermined amount of time since the decrease start time, is subtracted from an output signal resulting from the cuff pressure signal passing through the A/D conversion unit after the second time.

With the disclosed blood pressure measurement apparatus, the first time is a time that is after the increase start time, and the second time is a time that is after the decrease start time.

With the disclosed blood pressure measurement apparatus, the first time is the increase start time, and the second time is the decrease start time.

The disclosed blood pressure measurement apparatus includes: a subtraction unit that subtracts the output signal of the digital filter that corresponds to the cuff pressure signal detected at any time, from the output signal of the A/D conversion unit that corresponds to the cuff pressure signal detected at that time; and a change speed calculation unit that uses the output signal of the subtraction unit to calculate the change speed of the pressurizing pressure.

With the disclosed blood pressure measurement apparatus, the analog filter is a first-order high-pass filter or band-pass filter, and the digital filter is a first-order high-pass filter or band-pass filter.

With the disclosed blood pressure measurement apparatus, the predetermined amount of time is an amount of time that is shorter than the transient response period of the analog filter.

The disclosed pulse wave extraction method includes: a pressurizing pressure adjustment step of changing a pressure with which a cuff attached at a measurement site of a body pressurizes the measurement site; a cuff pressure detection step of detecting pressure in the cuff in a period of changing the pressurizing pressure as an analog cuff pressure signal; and a pulse wave detection step of detecting, in the cuff pressure signal, a pulse wave, which is a pressure component that is superimposed on the pressurizing pressure in synchronization with a pulse of the body, wherein the pulse wave detection step includes a step of extracting a high-frequency component from the cuff pressure signal by passing the cuff pressure signal through an analog filter, a step of converting, into a digital signal, the cuff pressure signal resulting from passing through the analog filter, a subtraction processing step of performing subtraction processing on the digital signal, and a step of extracting a high-frequency component by performing digital filter processing on a signal resulting from the processing of the subtraction processing step, and in the subtraction processing step, at least one of first subtraction processing in which a first signal, which is a signal resulting from the cuff pressure signal passing through the A/D conversion unit at a first time, which is any time in a period from an increase start time at which the pressurizing pressure starts increasing to a time at the elapse of a pre-determined amount of time since the increase start time, is subtracted from an output signal resulting from the cuff pressure signal passing through the A/D conversion unit in a period from the first time to a decrease start time at which the pressurizing pressure changes from increasing to decreasing, and second subtraction processing in which a second signal, which is a signal resulting from the cuff pressure signal passing through the A/D conversion unit at a second time, which is any time in a period from the decrease start time to a time at the elapse of a predetermined amount of time since the decrease start time, is subtracted from an output signal resulting from the cuff pressure signal passing through the A/D conversion unit after the second time is performed.

INDUSTRIAL APPLICABILITY

One or more embodiments of the claimed invention can be applied to a home-use blood pressure meter, for example, and is useful for managing the health of a user.

Although the claimed invention has been described in detail and with reference to a specific embodiment, it is clear to a person skilled in the art that various modifications and amendments can be added in accordance with one or more embodiments of the claimed invention without straying from the spirit and scope of the claimed invention. The present application is based on Japanese Patent Application (JP 2012-211138) filed Sep. 25, 2012, which is incorporated for reference herein.

REFERENCE NUMERALS LIST

1 Blood pressure measurement apparatus
10 Main body portion
30 Cuff
18 CPU
23 Pulse wave detection unit
232 First-order analog high-pass filter 233 A/D conversion unit
234 Signal storage unit
235 Pulse wave subtraction unit
236 First-order digital high-pass filter
181 Blood pressure determination unit
182 Inflation (deflation) speed calculation unit
183 CPU subtraction unit

The invention claimed is:

1. A blood pressure measurement apparatus comprising:
a cuff configured to be attached at a measurement site of a body;
a pressurizing pressure adjustment unit comprising: a pump; a valve; a pump drive circuit; and a valve drive circuit, the pressurizing pressure adjustment unit being configured to change a pressure with which the cuff pressurizes the measurement site;
a pressure sensor that detects an analog cuff pressure signal by detecting a pressure in the cuff in a period of changing the pressurizing pressure;
a pulse wave detection unit that, based on the cuff pressure signal, detects a pulse wave, which is a pressure component that is superimposed on the pressurizing pressure in synchronization with a pulse of the body; and
a CPU that determines a measured blood pressure value using the amplitude value of the pulse wave detected by the pulse wave detection unit,
wherein the pulse wave detection unit comprises:
an analog filter that extracts a high-frequency component from the cuff pressure signal;
an A/D conversion unit that performs digital conversion on an output signal of the analog filter;
a memory that stores at least a first signal and a second signal;
a first subtraction unit that performs subtraction processing on the output signal of the A/D conversion unit; and
a digital filter that performs filter processing for extracting a high-frequency component on the signal resulting from the subtraction processing performed by the first subtraction unit,
wherein the first subtraction unit performs at least one of first subtraction processing in which the first signal, which results from the cuff pressure signal passing through the A/D conversion unit at a first time, which is any time in a period from an increase start time at which the pressurizing pressure starts increasing to a time at an elapse of a predetermined amount of time since the increase start time, is subtracted from an output signal resulting from the cuff pressure signal passing through the A/D conversion unit in a period from the first time to a decrease start time at which the pressurizing pressure changes from increasing to decreasing, and second subtraction processing in which the second signal, which results from the cuff pressure signal passing through the A/D conversion unit at a second time, which is any time in a period from the decrease start time to a time at an elapse of a predetermined amount of time since the decrease start time, is subtracted from an output signal resulting from the cuff pressure signal passing through the A/D conversion unit after the second time, and
wherein the memory and the first subtraction unit shorten a transient response period of the digital filter based on the at least one of the first subtraction processing and the second subtraction processing, and based on starting the filter processing of the digital filter after the predetermined amount of time since at least one of the increase start time and the decrease start time.

2. The blood pressure measurement apparatus according to claim 1,
wherein the first time is a time that is after the increase start time, and
wherein the second time is a time that is after the decrease start time.

3. The blood pressure measurement apparatus according to claim 2, further comprising:
a second subtraction unit that subtracts the output signal of the digital filter that corresponds to the cuff pressure signal detected at any time, from the output signal of the A/D conversion unit that corresponds to the cuff pressure signal detected at that time; and
a change speed calculation unit that uses the output signal of the second subtraction unit to calculate the change speed of the pressurizing pressure.

4. The blood pressure measurement apparatus according to claim 2,
wherein the analog filter is a first-order high-pass filter or band-pass filter, and the digital filter is a first-order high-pass filter or band-pass filter.

5. The blood pressure measurement apparatus according to claim 2,
wherein the predetermined amount of time is an amount of time that is shorter than the transient response period of the analog filter.

6. The blood pressure measurement apparatus according to claim 1,
wherein the first time is the increase start time, and
wherein the second time is the decrease start time.

7. The blood pressure measurement apparatus according to claim 6, further comprising:
a second subtraction unit that subtracts the output signal of the digital filter that corresponds to the cuff pressure signal detected at any time, from the output signal of the A/D conversion unit that corresponds to the cuff pressure signal detected at that time; and
a change speed calculation unit that uses the output signal of the second subtraction unit to calculate the change speed of the pressurizing pressure.

8. The blood pressure measurement apparatus according to claim 6,
wherein the analog filter is a first-order high-pass filter or band-pass filter, and the digital filter is a first-order high-pass filter or band-pass filter.

9. The blood pressure measurement apparatus according to claim 6,
wherein the predetermined amount of time is an amount of time that is shorter than the transient response period of the analog filter.

10. The blood pressure measurement apparatus according to claim 1, further comprising:
a second subtraction unit that subtracts the output signal of the digital filter that corresponds to the cuff pressure signal detected at any time, from the output signal of the A/D conversion unit that corresponds to the cuff pressure signal detected at that time; and
a change speed calculation unit that uses the output signal of the second subtraction unit to calculate the change speed of the pressurizing pressure.

11. The blood pressure measurement apparatus according to claim 10,
wherein the analog filter is a first-order high-pass filter or band-pass filter, and the digital filter is a first-order high-pass filter or band-pass filter.

12. The blood pressure measurement apparatus according to claim 10,
wherein the predetermined amount of time is an amount of time that is shorter than the transient response period of the analog filter.

13. The blood pressure measurement apparatus according to claim 1,
wherein the analog filter is a first-order high-pass filter or band-pass filter, and the digital filter is a first-order high-pass filter or band-pass filter.

14. The blood pressure measurement apparatus according to claim 13,
wherein the predetermined amount of time is an amount of time that is shorter than the transient response period of the analog filter.

15. The blood pressure measurement apparatus according to claim 1,
wherein the predetermined amount of time is an amount of time that is shorter than the transient response period of the analog filter.

16. A pulse wave detection method comprising:
a pressurizing pressure adjustment step of changing a pressure with which a cuff attached at a measurement site of a body pressurizes the measurement site;
a cuff pressure detection step of detecting pressure in the cuff in a period of changing the pressurizing pressure as an analog cuff pressure signal; and
a pulse wave detection step of detecting, in the cuff pressure signal, a pulse wave, which is a pressure component that is superimposed on the pressurizing pressure in synchronization with a pulse of the body,
wherein the pulse wave detection step comprises:
a step of extracting a high-frequency component from the cuff pressure signal by passing the cuff pressure signal through an analog filter;
a step of converting, into a digital signal by an A/D conversion unit, the cuff pressure signal resulting from passing through the analog filter;
a step of storing at least a first signal and a second signal in a memory;
a first subtraction step of performing subtraction processing on the digital signal; and
a step of extracting a high-frequency component by using a digital filter to perform digital filter processing on a signal resulting from the processing of the first subtraction step,
wherein in the first subtraction step, at least one of first subtraction processing in which the first signal, which results from the cuff pressure signal passing through the A/D conversion unit at a first time, which is any time in a period from an increase start time at which the pressurizing pressure starts increasing to a time at an elapse of a predetermined amount of time since the increase start time, is subtracted from an output signal resulting from the cuff pressure signal passing through the A/D conversion unit in a period from the first time to a decrease start time at which the pressurizing pressure changes from increasing to decreasing, and second subtraction processing in which the second signal, which results from the cuff pressure signal passing through the A/D conversion unit at a second time, which is any time in a period from the decrease start time to a time at an elapse of a predetermined amount of time since the decrease start time, is subtracted from an output signal resulting from the cuff pressure signal passing through the A/D conversion unit after the second time is performed, and
wherein the memory of the storing step and the first subtraction step shorten a transient response period of the digital filter based on the at least one of the first subtraction processing and the second subtraction processing, and based on starting the filter processing of the digital filter after the predetermined amount of time since at least one of the increase start time and the decrease start time.

* * * * *